(12) United States Patent
Graham

(10) Patent No.: US 8,926,612 B2
(45) Date of Patent: Jan. 6, 2015

(54) ARTHRODESIS APPARATUS AND METHOD

(71) Applicant: The Cleveland Clinic Foundation, Cleveland, OH (US)

(72) Inventor: Thomas J. Graham, Novelty, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/791,133

(22) Filed: Mar. 8, 2013

(65) Prior Publication Data

US 2013/0237987 A1  Sep. 12, 2013

Related U.S. Application Data

(60) Provisional application No. 61/608,191, filed on Mar. 8, 2012.

(51) Int. Cl.
  *A61B 17/56* (2006.01)
  *A61B 17/72* (2006.01)
  *A61B 17/17* (2006.01)
  *A61B 17/15* (2006.01)
  *A61B 17/84* (2006.01)

(52) U.S. Cl.
  CPC ............. *A61B 17/7225* (2013.01); *A61B 17/17* (2013.01); *A61B 17/151* (2013.01); *A61B 17/7233* (2013.01); *A61B 17/842* (2013.01)
  USPC .......................................................... 606/64

(58) Field of Classification Search
  USPC ........................... 606/62–68, 86 R; 623/21.9, 623/21.15–21.17
  See application file for complete search history.

(56) References Cited

U.S. PATENT DOCUMENTS

| | | | |
|---|---|---|---|
| 3,824,631 A | 7/1974 | Burstein et al. | |
| 5,092,896 A | 3/1992 | Meuli et al. | |
| 6,045,551 A * | 4/2000 | Bonutti | 606/60 |
| 7,041,106 B1 | 5/2006 | Carver et al. | |
| 2004/0199254 A1 | 10/2004 | Louis et al. | |
| 2005/0171544 A1* | 8/2005 | Falkner, Jr. | 606/69 |
| 2009/0210016 A1 | 8/2009 | Champagne | |
| 2010/0057214 A1 | 3/2010 | Graham et al. | |
| 2011/0082508 A1 | 4/2011 | Reed | |

* cited by examiner

*Primary Examiner* — Mary Hoffman
*Assistant Examiner* — Tara R Carter
(74) *Attorney, Agent, or Firm* — Tarolli, Sundheim, Covell & Tummino LLP

(57) ABSTRACT

An apparatus to promote bone fusion between portions of bone tissue comprises a bone engagement member and a flexible retention member. The bone engagement member comprises (a) an extramedullary bone contacting main body with a first surface defining a hole in the main body and (b) an intramedullary bone engaging projection extending from the main body. The projection engages the intramedullary portions of at least one the portions of bone tissue. The projection includes a second surface that defines a retention passage in the projection. The retention passage is spaced away from the hole and oriented transversely relative to the hole. The flexible retention member is configured and dimensioned to extend through the retention passage and into the hole to help retain the projection in intramedullary engagement with the at least one of the portions of bone tissue.

10 Claims, 7 Drawing Sheets

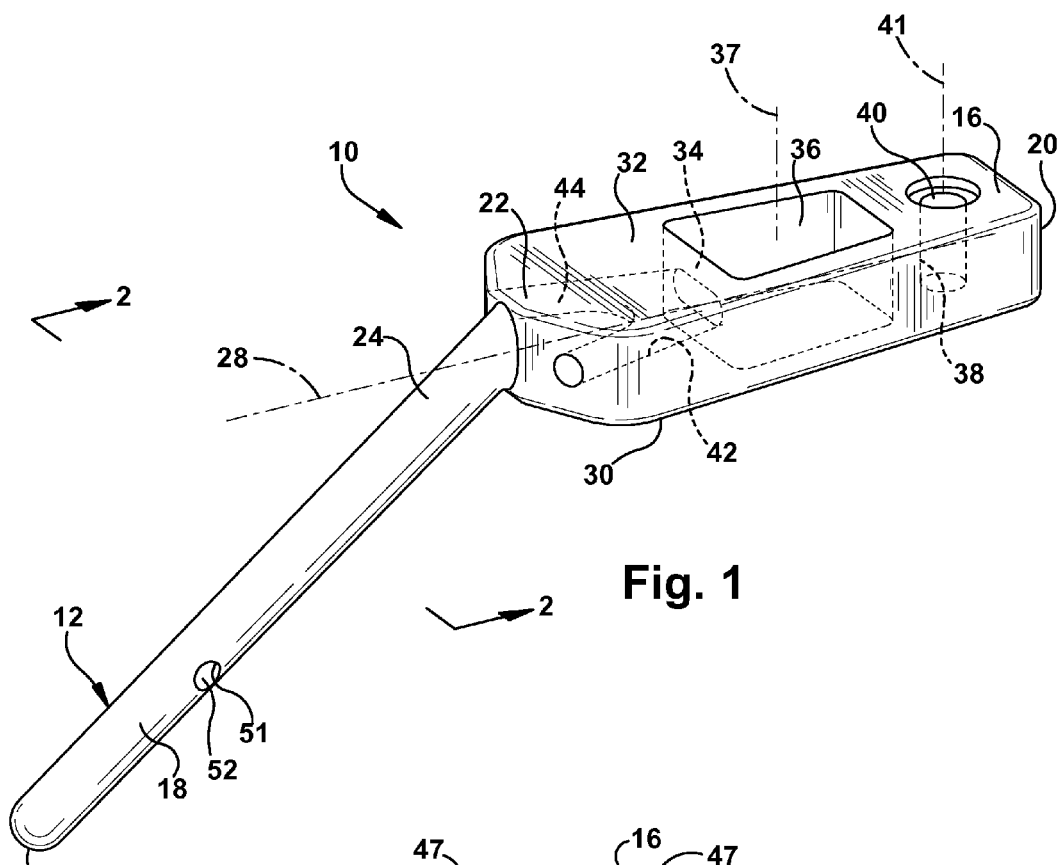
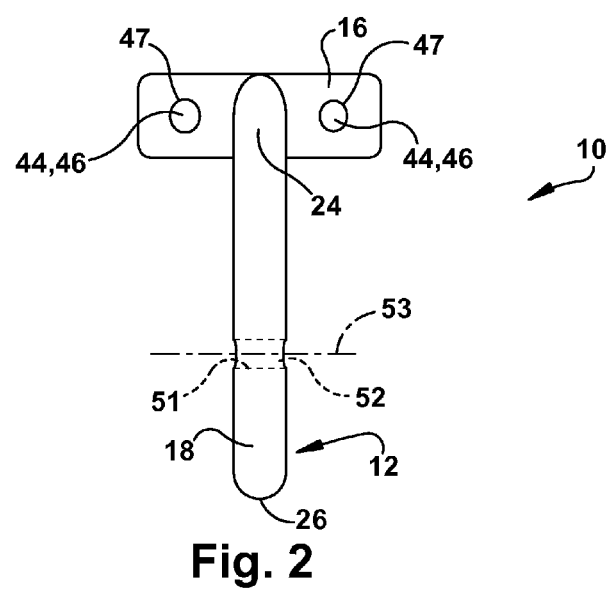

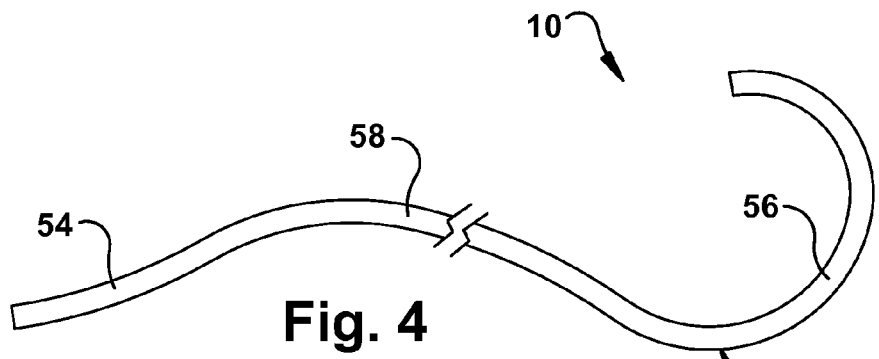
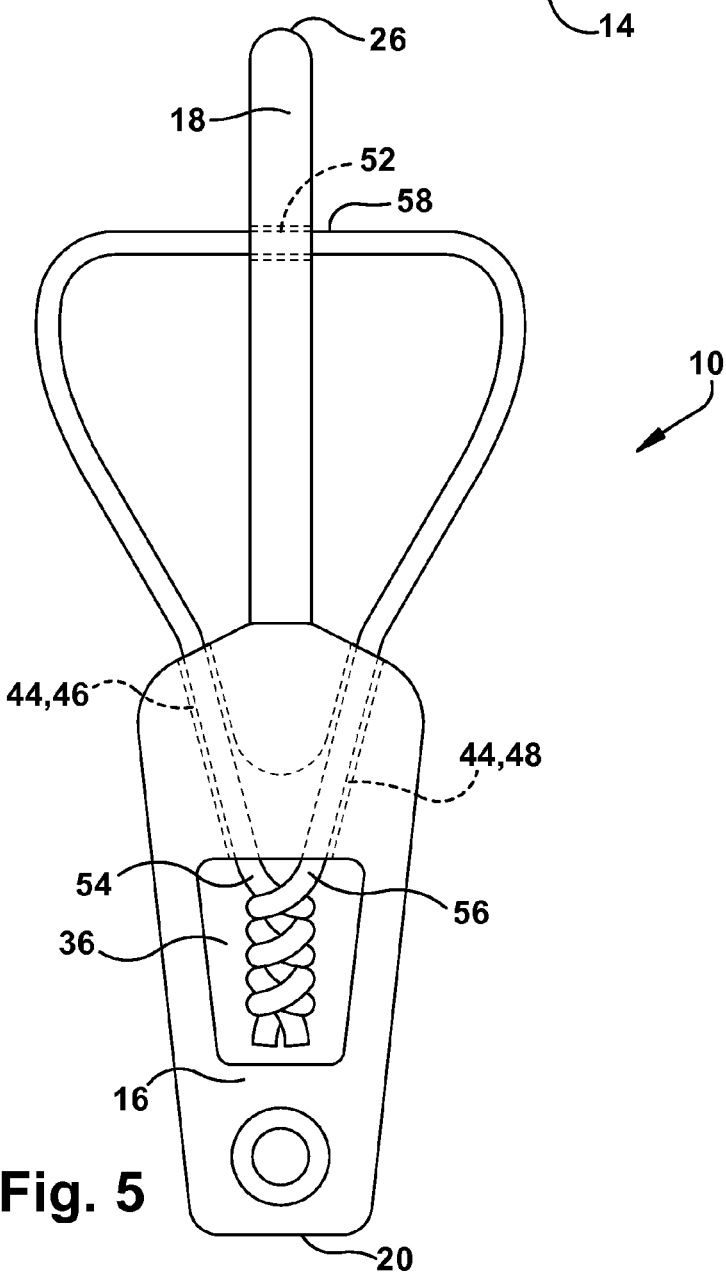

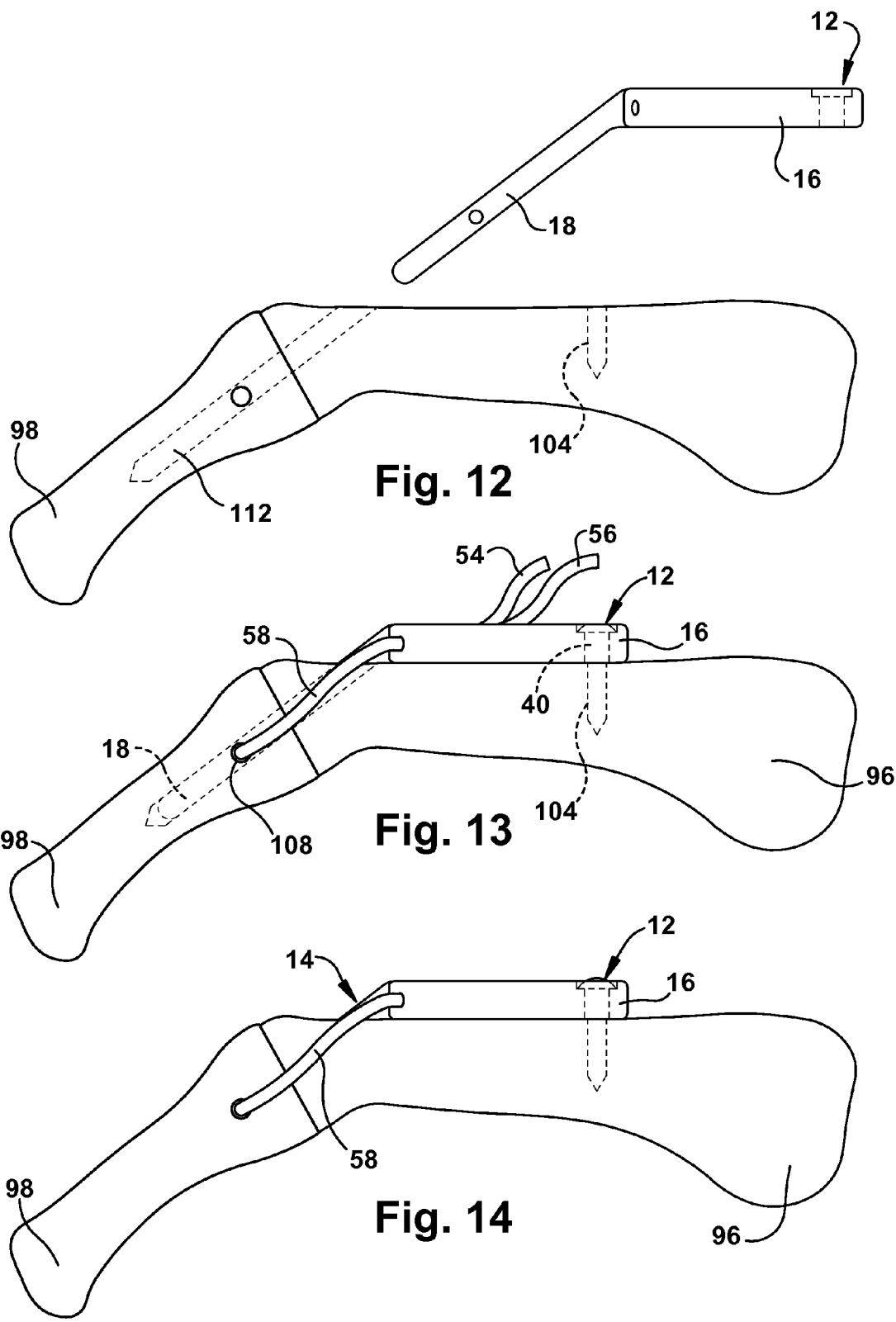

ARTHRODESIS APPARATUS AND METHOD

RELATED APPLICATION

This application claims the benefit of U.S. Provisional Patent Application Ser. No. 61/608,191, filed Mar. 8, 2012, the entirety of which is hereby incorporated by reference for all purposes.

TECHNICAL FIELD OF THE INVENTION

The present invention relates to an apparatus to promote fusion between portions of bone tissue and to a method of using such an apparatus and, more particularly, to an arthrodesis apparatus to apply compressive force to bones and to a method of using such an apparatus.

BACKGROUND OF THE INVENTION

Arthrodesis or joint fusion is a widely used procedure to provide pain relief, restore skeletal stability, and improve bone alignment at a joint between two bones. One approach for implementing arthrodesis is to attach a rigid member to both bones so as to hold the bones together in a position favoring bone fusion. Arthrodesis may involve cutting pieces from the bones to help achieve a desired alignment of the bones following joint fusion.

SUMMARY OF THE INVENTION

The present invention is directed to an apparatus to promote fusion between portions of bone tissue and to a method of using such an apparatus and, more particularly, to an arthrodesis apparatus to apply compressive force to bones and to a method of using such an apparatus.

In accordance with an embodiment of the present invention, an apparatus to promote fusion between portions of bone tissue comprises a bone engagement member. The bone engagement member includes an extramedullary bone contacting main body with a first surface defining a hole in the main body. The bone engagement member also includes an intramedullary bone engaging projection extending from the main body for intramedullary engagement with at least one of the portions of bone tissue. The projection includes a second surface that defines a retention passage in the projection. The retention passage is spaced away from the hole in the main body and is oriented transversely relative to the hole in the main body. The apparatus also comprises a flexible retention member. The retention member is configured and dimensioned to extend through the retention passage and into the hole in the main body of the bone engagement member to help retain the projection in intramedullary engagement with the at least one portion of bone tissue.

In accordance with another embodiment of the present invention, a method for promoting fusion between portions of bone tissue comprising the step of inserting a projection of a bone engagement member into an intramedullary portion of a first portion of bone tissue. The bone engagement member includes (i) an extramedullary bone contacting main body with a first surface defining a hole in the main body and (ii) an intramedullary bone engaging projection extending from the main body. The projection includes a second surface defining a retention passage in the projection. The retention passage is spaced from the hole and is oriented transversely relative to the hole. The method also comprises the steps of positioning the main body of the bone engagement member on an extramedullary surface of a second portion of bone tissue and inserting a flexible retention member through the second portion of bone tissue and through the retention passage. The method further comprises the step of securing together opposite end portions of the flexible retention member within the hole in the main body of the bone engagement member to help retain the first and second portions of bone tissue in contact with each other to promote fusion between the first and second portions of bone tissue.

In accordance with yet another embodiment of the present invention, a bone preparation apparatus to prepare portions of bone tissue to promote fusion between the portions of bone tissue comprises a tool template and a cutting guide. The tool template includes a main body with a first surface and a second surface spaced apart from the first surface and is presented in a direction opposite a direction in which the first surface is presented. The first surface is a bone contacting surface. A tubular barrel extends from the second surface of the main body at a predetermined angle. The tubular barrel includes a passage that extends through at least a portion of a length of the tubular barrel. The cutting guide includes a guide surface and a peg oriented at a predetermined angle to the guide surface. The peg is configured and dimensioned to be received in the passage of the tubular barrel of the tool template.

In accordance with yet a further embodiment of the present invention, a method for method of using a bone preparation apparatus to prepare portions of bone tissue to promote fusion between the portions of bone tissue comprises the step of mounting a tool template on an extramedullary part of a portion of bone tissue. The tool template includes a main body and a tubular barrel. The main body has a first surface and a second surface spaced apart from the first surface and presented in a direction opposite a direction in which the first surface is presented. The first surface is mounted in contact with the extramedullary part of the portion of bone tissue. The tubular barrel extends from the second surface of the main body at a predetermined angle. The tubular barrel includes a passage that extends through at least a portion of a length of the tubular barrel. The method also comprises the step of mounting a cutting guide on the tool template. The cutting guide includes (i) a guide surface and (ii) a peg oriented a predetermined angle to the guide surface. The peg is received in the passage of the tubular barrel of the tool template when the cutting guide is mounted on the tool template. The method further comprises the step of guiding a cutting instrument with the guide surface of the cutting guide so as to cut the portion of bone tissue along a plane established by (i) the predetermined angle at which the tubular barrel extends from the second surface of the main body and (ii) the predetermined angle at which the peg is oriented to the guide surface.

BRIEF DESCRIPTION OF THE DRAWINGS

The foregoing and other features and advantages of the present invention will become apparent to one skilled in the art upon consideration of the following description of the invention and the accompanying drawings, in which:

FIG. 1 is a side view of a bone engagement member, in accordance with the present invention;

FIG. 2 is an end view of the bone engagement member of FIG. 1, taken in the direction of the arrows 2-2 in FIG. 1;

FIG. 4 is a plan view of a flexible retention member in accordance with the present invention;

FIG. 5 is a top view of the bone engagement member of FIG. 3 and the flexible retention member of FIG. 4 assembled together;

FIG. 12 is a schematic side view showing the bone engagement member of FIG. 3 and the flexible retention member of FIG. 4 in a first stage of installation in first and second bones;

FIG. 13 is a schematic side view showing the bone engagement member of FIG. 3 and the flexible retention member of FIG. 4 in a second stage of installation in first and second bones;

FIG. 14 is a schematic side view showing the bone engagement member of FIG. 3 and the flexible retention member of FIG. 4 in a third stage of installation in first and second bones;

DETAILED DESCRIPTION OF THE INVENTION

Figure 3:
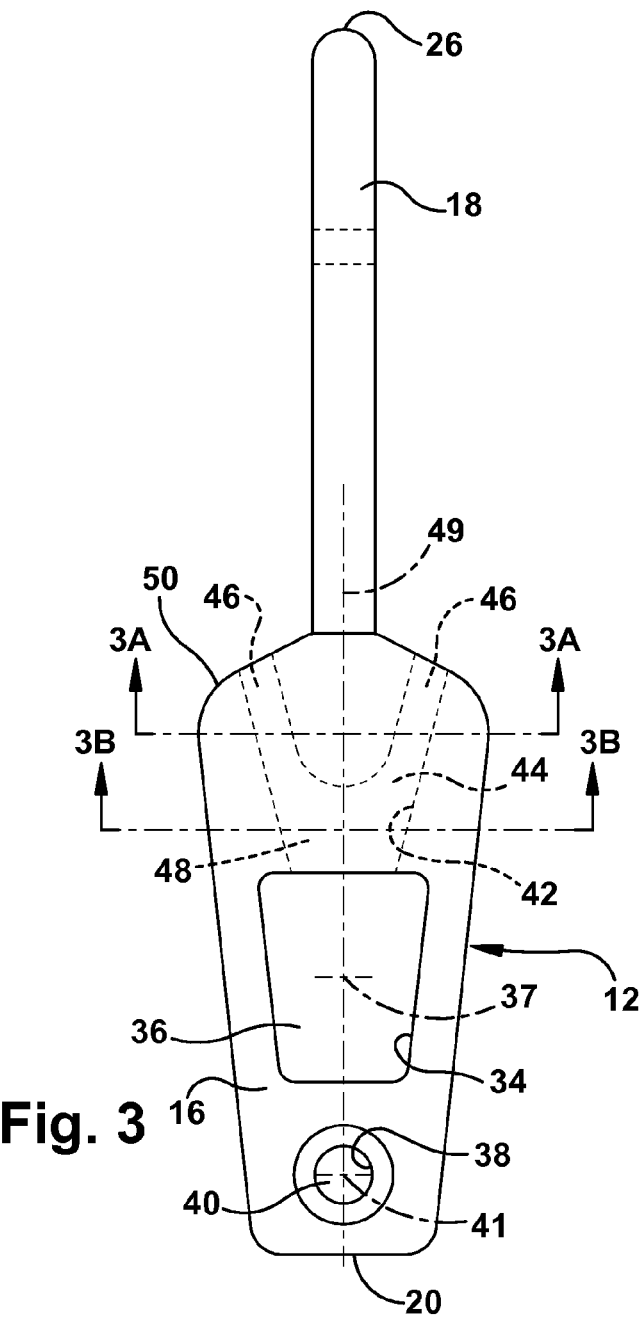
FIG. 3 is a top view of the bone engagement member of FIG. 1.
Figure 3A:
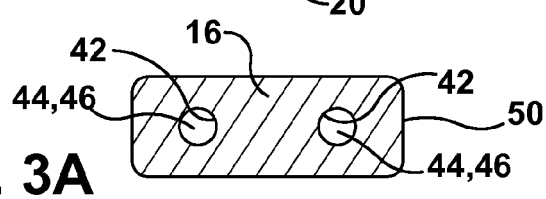
FIG. 3A is a sectional view taken generally along line 3A-3A of FIG. 3.
Figure 3B:
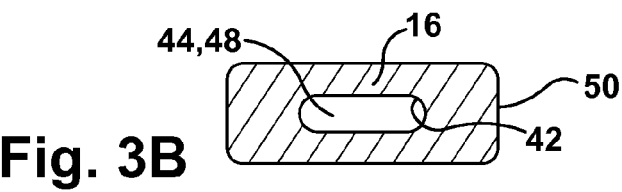
FIG. 3B is a sectional view taken generally along line 3B-3B of FIG. 3.

FIGS. 1-5 show an apparatus 10 in accordance with an example of the present invention. The apparatus 10 comprises a bone engagement member 12 (FIGS. 1-3) and a flexible retention member 14 (FIG. 4). The bone engagement member 12 is made of a relatively rigid bio-compatible material, such as medical grade stainless steel or titanium. The bone engagement member 12 includes a main body 16 and a projection 18. The main body 16 has a first end 20 and an opposite second end 22. As shown, the first end 20 is a proximal end of the main body 16, but the first end may alternatively be a distal end of the main body. Similarly, as shown, the second end 22 is a distal end of the main body 16, but the second end may alternatively be a proximal end of the main body. The projection 18 also has a first end 24 and a second end 26. The first end 24 of the projection 18 adjoins and is connected to the second end 22 of the main body 16. Although the projection 18 may be formed as a separate member and subsequently connected to the main body 16, the projection, as shown, is formed in one piece with the main body. As best shown in FIG. 1, the projection 18 extends away from the main body 16 at an angle relative to a central longitudinal axis 28 of the main body 16. The predetermined angle may be any desired angle, such as 20°, 30°, 40°, or 50°, at which two bones other portion of bone tissue are to be fused to one another.

An inward facing surface 30 of the main body 16 is configured to be presented toward an external surface or extramedullary portion of a bone or other portion of bone tissue. The inward facing surface 30 extends along the length of the main body 16 between its first and second ends 20 and 22. The inward facing surface 30 also extends across the width of the main body 16. Opposite the inward facing surface 30 is an outward facing surface 32, which is configured to be presented away from the external surface or extramedullary portion of a bone or other portion of bone tissue. The outward facing surface 32 extends along the length of the main body 16 between its first and second ends 20 and 22. The outward facing surface 32 also extends across the width of the main body 16.

A first internal surface 34 of the main body 16 extends around and along a central longitudinal axis 37 and defines a hole 36 in the main body 16. The central longitudinal axis 37 and the hole 36 extend transverse to the central longitudinal axis 28 of the main body 16. As shown in FIG. 1, the first internal surface 34 and the hole 36 extend from the outward facing surface 32 completely through the main body 16 to the inward facing surface 30. The first internal surface 34 and the hole 36 may, however, extend from the outward facing surface 32 only part way toward the inward facing surface 30 and only part way through the main body 16. The hole 36 is disposed between the first and second ends 20 and 22 of the main body 16.

A second internal surface 38 of the main body 16 of the bone engagement member 12 extends around and along a central longitudinal axis 41 and defines an aperture 40 in the main body 16. The central longitudinal axis 41 and the aperture 40 extend transverse to the central longitudinal axis 28 of the main body 16. The second internal surface 38 and the aperture 40 extend from the outward facing surface 32 completely through the main body 16 to the inward facing surface 30. The aperture 40 is located adjacent the first end 20 of the main body between the first end and the hole 36. The aperture 40 is configured and dimensioned to receive a fastener (not shown in FIGS. 1-5).

A third internal surface 42 of the main body 16 of the bone engagement member 12 defines a Y-shaped connecting passage 44, which is best seen in FIG. 3. The connecting passage 44 includes two first portions 46 and a second portion 48. The third internal surface 42 extends between an outer surface 50 of the main body 16 and the first internal surface 34 of the main body. The connecting passage 44 thus extends across and through a portion of the main body 16 and terminates in the hole 36. More particularly, two openings 47 are formed in the outer surface 50 of the main body 16 adjacent the second end 22 of the main body. The openings 47 are spaced apart so that the first end 24 of the projection 18 is disposed between the openings 47. Each of the first portions 46 of the connecting passage 44 extends from a corresponding opening 47 in the outer surface 50 of the main body 16 to one end of the second portion 48 of the connecting passage. The second portion 48 of the connecting passage 44 extends from the first portions 46 to the first internal surface 34 and the hole 36. In defining the second portion 48 of the connecting passage 44, the third internal surface 42 extends around and along a central longitudinal axis 49. The central longitudinal axis 49 and the second portion 48 of the connecting passage 44 are coaxial with the central longitudinal axis 28 of the main body 16 and transverse to the central longitudinal axis 37 through the hole 36.

As shown in FIGS. 1 and 5, the projection 18 of the bone engagement member 12 has an internal surface 51 that extends around and along a central longitudinal axis 53. The internal surface 51 defines a retention passage 52 in the projection 18. The central longitudinal axis 53 and the retention passage 52 extend transverse to the central longitudinal axis 28 of the main body 16 of the bone engagement member 12, transverse to the central longitudinal axis 37 through the hole 36, and transverse to the central longitudinal axis 49 through the second portion 48 of the connecting passage 44. The retention passage 52 is disposed between the first end 24 and the second end 26 of the projection 18. The retention passage 52 is spaced away from the hole 36 and the connecting passage 44.

The retention member 14 includes a first end portion 54, an opposite second end portion 56, and an intermediate portion 58 that connects the end portions 54 and 56 to each other. The retention member 14 is configured and dimensioned to pass readily through the retention passage 52 and the connecting passage 44, in a manner explained below. In one example, the retention member 14 may be a Kirschner wire or K-wire made of steel. The retention member 14 may, however, may have a variety of constructions that permit the retention member to be strong and flexible and thus capable of being manipulated as described below. For example, the retention member 14 may be fabricated of materials other than steel that provide the desired strength and flexibility to be used as described below. The retention member may also be formed of a twisted strand of metal or polymer fibers and may optionally be coated with a bio-compatible polymer.

The retention member 14 is assembled together with and cooperates with the bone engagement member 12 to help retain the bone engagement member 12 in position. The retention member 14 helps to apply compressive force to bones or other portions of bone tissue in which the bone engagement member 12 is installed or implanted. When the retention member 14 is assembled together with the bone engagement member 12, the intermediate portion 58 of the retention member extends through the retention passage 52 of the projection 18, as shown in FIG. 5. The end portions 54, 56 of the flexible retention member 14 extend through the Y-shaped connecting passage 44 and into the hole 36 of the main body 16. The end portions 54, 56 of the flexible retention member 14 are twisted together or otherwise secured to each other within the hole 36.

Figure 6:
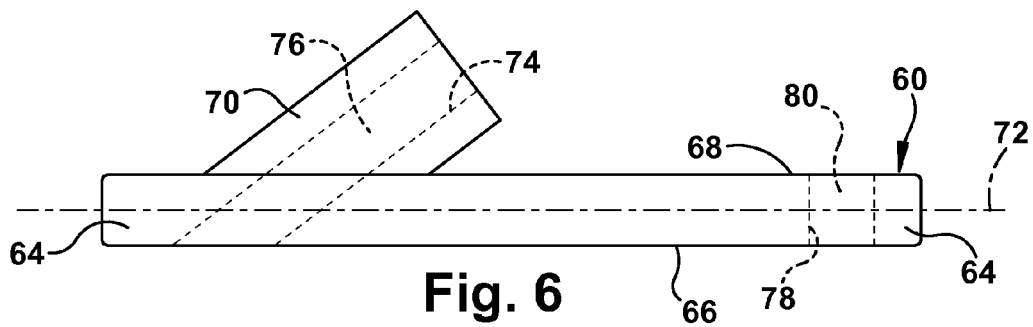
FIG. 6 is a side view of a tool template used to guide a drilling tool and to align a cutting guide for preparing a bone to receive the bone engagement member of FIG. 3.
Figure 7:
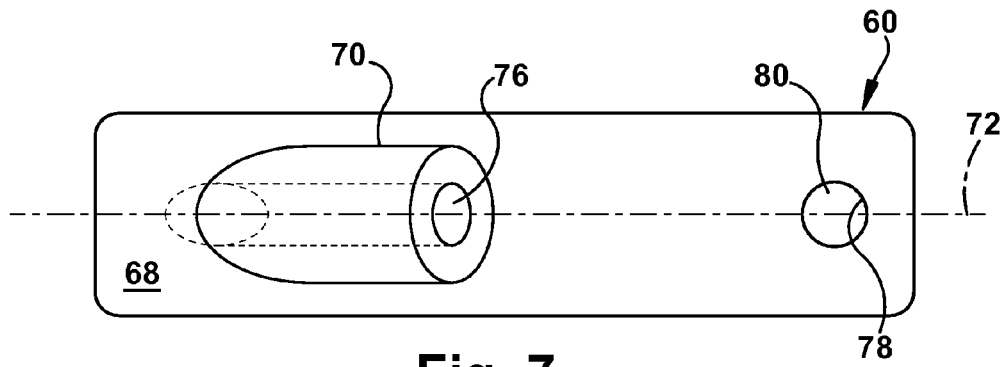
FIG. 7 is a top view of the tool template of FIG. 6.
Figure 8:
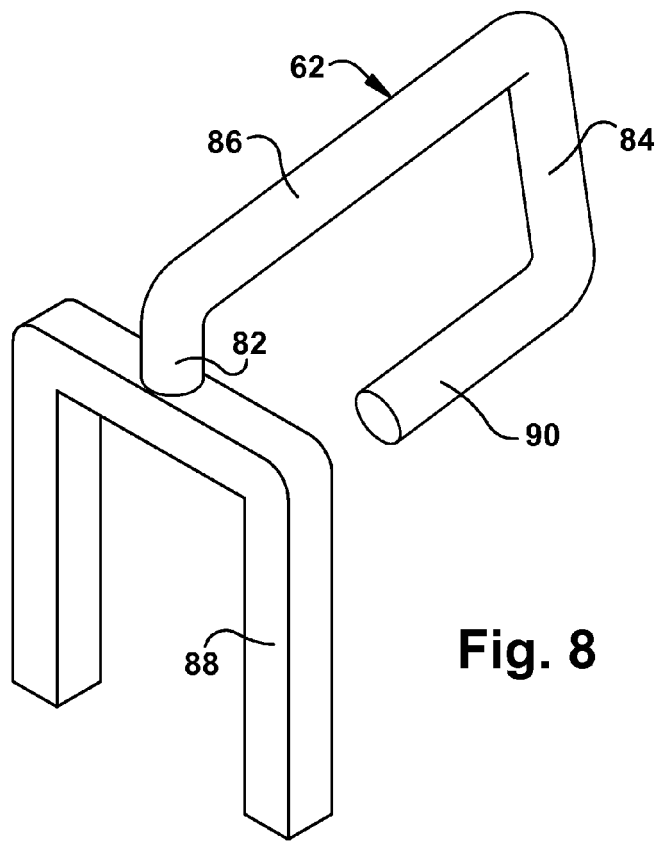
FIG. 8 is a side view of a cutting guide used to determine a cutting line across a bone.

The apparatus 10 is used to promote fusion between portions of bone tissue. More particularly, the apparatus 10 may be used in arthrodesis to promote fusion between bones on opposed sides of a joint. Prior to using the apparatus 10 in an arthrodesis, the bones to be fused require preparation to receive the apparatus and achieve a desired outcome. A tool template 60 and a cutting guide 62, as shown in FIGS. 6-8, may be used in such preparation.

Figure 9:
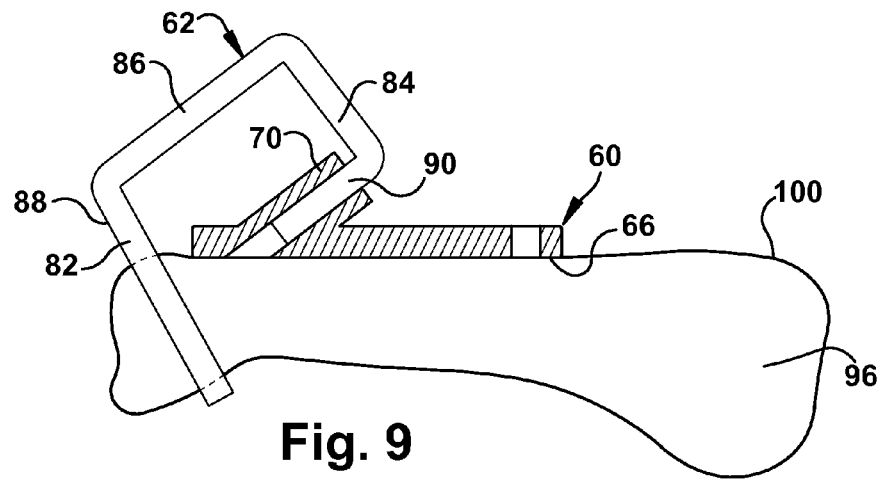
FIG. 9 is a schematic side view showing the cutting guide of FIG. 8 engaging the tool template of FIG. 6.

The tool template 60 (FIGS. 6-7) includes a main body 64. The main body 64 has a bone contacting surface 66 for presentation toward a bone and an opposite surface 68 for presentation away from the bone. Both the bone contacting surface 66 and the opposite surface 68 extend along the length of the main body 64 between its opposite ends. Both the bone contacting surface 66 and the opposite surface 68 also extend across the width of the main body 64. A tubular barrel 70 extends from the surface 68 of the tool template. The barrel 70 is oriented at a predetermined angle relative to a central longitudinal axis 72 of the main body 64. The predetermined angle may be any desired angle, such as 20°, 30°, 40°, or 50°, provided the predetermined angle is substantially the same as the predetermined angle at which a projection 18 of a bone engagement member 12 extends away from a main body 16 of the bone engagement member. The barrel 70 includes a surface 74 that defines a passage 76 extending lengthwise of the barrel 70. The passage 76 extends through the length of the barrel 70 and opens onto the bone contacting surface 66. The passage 76 is configured and dimensioned to receive a tool, such as a drill D (FIG. 11), and, at other times, a portion of the cutting guide 62 (FIG. 9). The main body 64 of the tool template 60 also includes a surface 78 that defines a hole 80 through the main body. The hole 80 is spaced away from the barrel 70 and is dimensioned to receive a tool, such as the drill D (FIG. 10), and, at other times, a fastener TF (FIG. 11).

The cutting guide 62 (FIG. 8) has a generally C-shaped or U-shaped configuration. More specifically, the cutting guide 62 includes a base portion 82, a head portion 84, and a connecting portion 86. The base portion 82 is bifurcated and has a bifurcated guide surface 88 for a saw (not shown) or other cutting tool. The connecting portion 86 joins the base portion 82 to the head portion 84 so as to provide the general U-shape. The head portion 84 includes an end fitting or peg 90 that is spaced apart or away from the connecting portion 86. The peg 90 thus is on one leg of the U-shaped cutting guide 62, and the guide surface 88 is on the opposite leg of the U-shaped cutting guide. The peg 90 projects away from the head portion 84 and is oriented at a predetermined angle relative to the guide surface 88 of the base portion. The predetermined angle may, for example, be 90°. Because the angle between the peg 90 and the guide surface 88 is predetermined, establishing the angular position of the peg 90 relative to a bone will also establish the angular position of the guide surface 88 relative to the bone. As will be explained below, the angular position of the peg 90 relative to a bone is determined by the angle at which the tubular barrel 70 of the tool template 60 is oriented relative to the central longitudinal axis 72 of the main body 64 of the tool template. The angular position of the guide surface 88 relative to the bone is thus determined by both (a) the angle at which the tubular barrel 70 of the tool template 60 is oriented relative to the central longitudinal axis 72 of the main body 64 of the tool template and (b) the angle at which the peg 90 is oriented relative to the guide surface 88 of the cutting guide 62.

Figure 10:
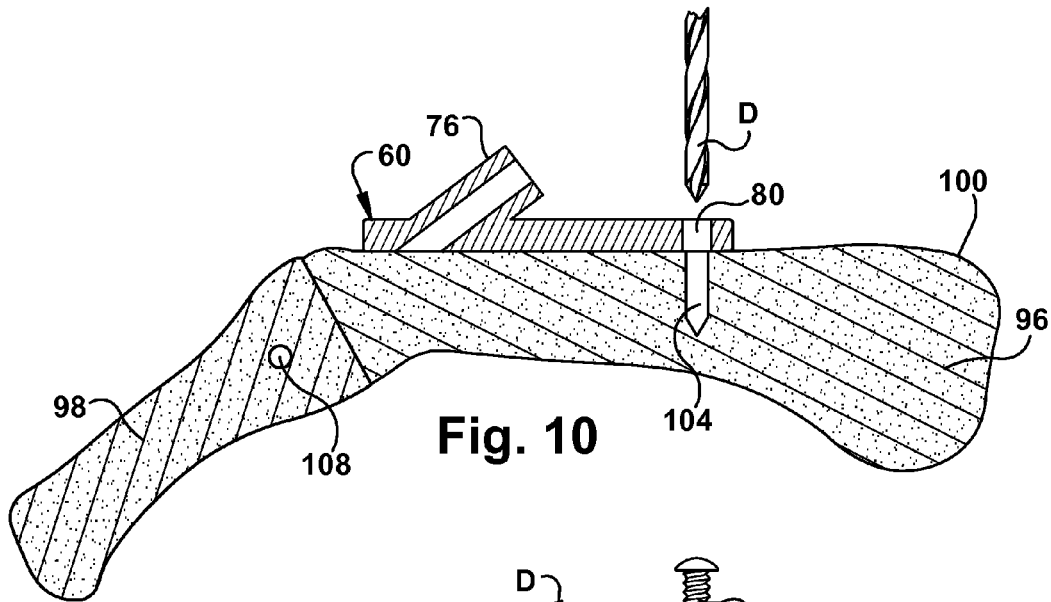
FIG. 10 is a schematic side view showing a first bone in contact with the tool template of FIG. 6.
Figure 11:
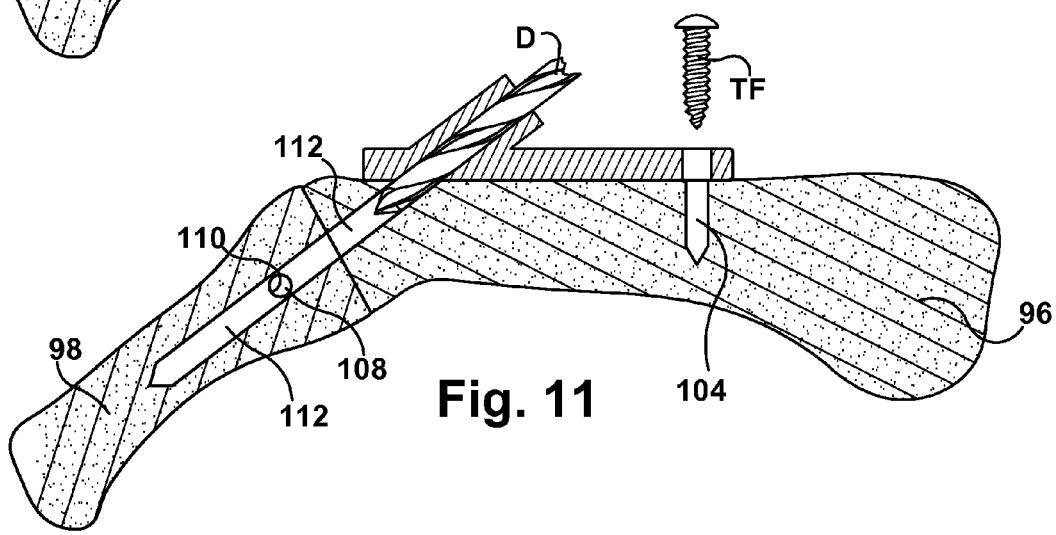
FIG. 11 is a schematic side view showing a drill engaging the tool template of FIG. 10 and passages formed in the intramedullary portions of first and second bones.

Three stages of a surgical procedure to prepare two adjacent phalangeal bones 96 and 98 for installation of the apparatus 10 are shown in FIGS. 9-11. As shown, the bone 96 is the proximal bone, and the bone 98 is the distal bone. Nonetheless, the bone 96 may be the distal bone and the bone 98 may be the proximal bone. The preparatory surgical procedure begins with the step of positioning the tool template 60 along an extramedullary portion or external surface 100 of the bone 96. In particular, the bone contacting surface 66 of the main body 64 of the tool template 60 contacts the external surface 100 of the bone 96.

After the tool template 60 is properly positioned, the preparatory surgical procedure continues with the step of positioning the cutting guide 62. The cutting guide 62 is used to help determine a cutting line or cutting plane along one or both of the bones 96, 98 to assist a surgeon in cutting a piece off one or both of the bones 96, 98. The head portion 84 of the cutting guide 62 is engaged with the tool template 60 by inserting the peg 90 into the passage 76 of the barrel 70 of the tool template 60, as shown in FIG. 9. When the peg 90 is inserted into the barrel 70, the bifurcated base portion 82, including the two bifurcations of the guide surface 88, of the cutting guide 62 is positioned adjacent two opposed sides or surfaces of the bone 96. In other words, a first bifurcation of the bifurcated guide surface 88 is positioned adjacent a first side of the bone 96, and a second bifurcation of the bifurcated guide surface is positioned adjacent a second side of the bone. The guide surface 88 is positioned immediately adjacent the bone 96 and spaced slightly away from the bone 98. Because the peg 90 and the guide surface 88 have a predetermined angular orientation, the position of the peg helps determine the position of the guide surface and the positions of cutting lines or cutting planes across the bones 96, 98.

With the base portion 82 and guide surface 88 properly positioned, the preparatory surgical procedure continues with the step of cutting a bone piece from the bone 96 using a cutting tool (not shown), such as a saw, along a cutting line and a cutting plane established by the guide surface 88. More particularly, the cutting line and cutting plane are established by (i) the predetermined angle at which the tubular barrel 70 extends from the surface 68 of the main body 64 of the tool template 60 and (ii) the predetermined angle at which the peg 90 of the cutting guide 62 is oriented to the guide surface 88. A surgeon cutting the bone 96 may cut the bone using the cutting tool either in contact with and following the guide surface 88 or simply following a cutting line established or marked using the guide surface.

A piece is also cut from the bone 98 using the cutting tool. Again, a surgeon cutting the bone 98 may cut the bone using the cutting tool either in contact with or following the guide surface 88 or simply following a cutting line established or marked using the guide surface. Because the guide surface 88 is initially spaced away from the bone 98, it may be necessary or desirable to move the tool template 60 longitudinally along the extramedullary portion or external surface 100 of the bone 96 in order to position the guide surface properly relative to the bone 98. Alternatively, it may be desirable to replace the cutting guide 62 with a similarly configured cutting guide (not shown) with a longer connecting portion 86 in order to place the guide surface 88 sufficiently close to the bone 98 without repositioning the tool template 60. Regardless of whether the tool template is repositioned or whether a second cutting guide 62 is used, the angle and position of the cutting line and/or cutting plane across the bone 98 are complementary to the angle and position of the cutting line and/or cutting plane across the bone 96. As a result of the complementary angles and positions, the bones 96 and 98 will mate and fuse together in a predetermined orientation.

The next step in the preparatory surgical procedure is to remove the cutting guide 62 from the tool template 60 while leaving the tool template in place along the extramedullary portion or external surface 100 of the bone 96. After removing the cutting guide 62, the preparatory surgical procedure continues with the step of forming a passage 104 in the bone 96, as shown in FIG. 10. The passage 104 is formed by inserting a tool, such as a drill D, into the hole 80 of the tool template 60 and forming the passage 104 into the intramedullary portion of the bone 96. The passage 104 is configured and dimensioned such that a fastener 106 (FIG. 15) can be used to secure the bone engagement member 12 in place on the extramedullary portion or external surface 100 of the bone 96. When the passage 104 is formed, the next step in the preparatory surgical procedure is to form a passage 108 in the bone 98 using a tool such as the drill D. The passage 108 is defined by an internal surface 110 in the bone 98. The passage 108 will receive the intermediate portion 58 of the retention member 14 and will be aligned with the retention passage 52 in the projection 18.

A second passage 112 is formed in both bones 96, 98 in the next step of the preparatory surgical procedure. In particular, the cut ends of the bones 96, 98 are placed together and aligned. The tool template 60 is temporarily secured in place along the extramedullary portion or external surface 100 of the bone 96 with a temporary fastener TF inserted through the hole 80 of the tool template and into the passage 104. As shown in FIG. 11, a tool, such as a drill D, is then inserted into the barrel 70 of the tool template 60 to form the second passage 112 in the intramedullary portions of both of the bones 96, 98. The outer diameter of the second passage 112 is dimensionally the same as or slightly larger than the outer diameter of the projection 18. The passage 108 in the bone 98 intersects the second passage 112.

With the bones 96, 98 prepared, the surgeon can begin a surgical procedure to install or implant the apparatus 10 (FIGS. 12-14) as an interphalangeal arthrodesis apparatus. The first step of the implantation surgical procedure is installing the bone engagement member 12. To install the bone engagement member 12, the projection 18 of the bone engagement member 12 is inserted into the second passage 112 and engages the intramedullary portions of the bones 96, 98. When the projection 18 is inserted into the second passage 112, the bone engagement member 12 is positioned such that the aperture 40 in the bone engagement member 12 is aligned with the passage 104. In addition, the retention passage 52 of the projection 18 is aligned with the passage 108 in the bone 98.

When the bone engagement member 12 is installed, the next step in the implantation surgical procedure is to install the retention member 14. One of the end portions 54, 56 of the retention member 14 is inserted through the passage 108 in the bone 98 and through the retention passage 52 in the projection 18. The retention member 14 is pulled through the passage 108 and the aligned retention passage 52 until the intermediate portion 58 of the retention member 14 is positioned with approximately equal lengths of the retention member on each side of the projection 18 and on each side of the bone 98. The end portions 54 and 56 of the retention member 14 are then inserted into the first portions 46 of the Y-shaped connecting passage 44 of the main body 16 of the bone engagement member 12. The end portions 54, 56 are pulled through the second portion 48 of the Y-shaped connecting passage 44 and into the hole 36 of the bone engagement member 12 (FIG. 13). The end portions 54, 56 are positioned in the hole 36 so that tips of the end portions 54, 56 extend out of the hole 36 and away from the bone engagement member 12 and the bones 96, 98. The end portions 54, 56 are then engaged with each other to help secure the bone engagement member 12 to the bones 96, 98 and to apply compressive force to the bones. The end portions 54, 56 can be twisted together, or can be joined together by other conventional methods. After being twisted or otherwise joined together, the end portions 54, 56 are trimmed to remove excess material and are tucked into the hole 36 (FIG. 14).

As the final step in the implantation surgical procedure, a bone screw or other fastener 106 is inserted into the aperture 40 in the main body 16 of the bone engagement member 12. The fastener 106 is screwed into the passage 104 in the bone 96 to help secure the bone engagement member 12 to the bone 96. The fully installed or implanted apparatus 10 is shown in FIG. 15.

Figures 15, 16:
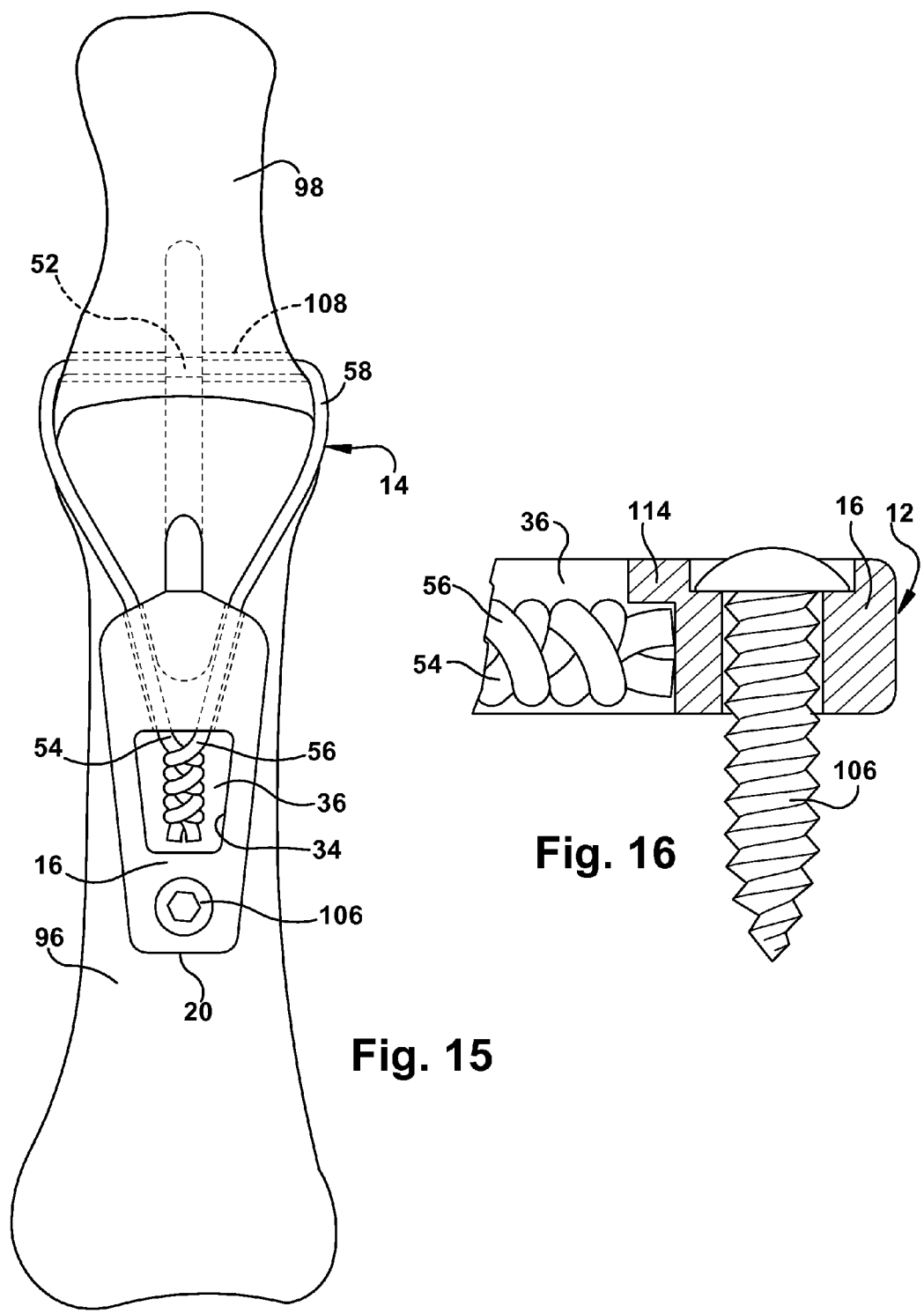
FIG. 15 is a schematic top view of the bone engagement member and flexible retention member of FIG. 14 fully installed in first and second bones.
FIG. 16 is a side view showing a modified bone engagement member in accordance with the present invention.

As shown in FIG. 16, the main body 16 of the bone engagement member 12 may include a flange 114 located adjacent the hole 36 in the main body. The flange 114 extends toward the central longitudinal axis 37 of the hole 36 and overlies a portion of the hole 36. In other words, the flange 114 lies or extends above the hole 36 and across a portion of the hole. In use, the flange 114 overlies, that is to say, lies or extends above and across, at least part of the engaged end portions 54, 56 of the flexible retention member 14 to help maintain the end portions 54, 56 within the hole 36 of the bone engagement member 12.

From the above description of the invention, those skilled in the art will perceive improvements, changes and modifications. Such improvements, changes, and/or modifications within the skill of the art are intended to be covered by the appended claims.

Having described the invention, the following is claimed:

1. An apparatus to promote fusion between portions of bone tissue comprising:

(a) a bone engagement member including:
  (i) an extramedullary bone contacting main body with a first surface extending around a first central longitudinal axis and defining a hole in the main body; and
  (ii) an intramedullary bone engaging projection extending from the main body for intramedullary engagement with at least one of the portions of bone tissue, the projection including a second surface defining a retention passage in the projection, the retention passage being spaced from the hole and being oriented transversely relative to the hole,
  the main body of the bone engagement member including a third surface extending along a length of the main body and across a width of the main body, the main body also including a fourth surface extending along the length of the main body and across the width of the main body, the fourth surface being spaced apart from the third surface and being presented in a direction opposite a direction in which the third surface is presented, the fourth surface being an extramedullary bone contacting surface, the first surface extending through the main body from the third surface toward the fourth surface,
  the main body of the bone engagement member further including a fifth surface extending around a second central longitudinal axis and defining a connecting passage, the connecting passage extending through the main body from an outer surface of the main body to the first surface and connecting with the hole, the second central longitudinal axis extending transverse to the first central longitudinal axis; and
(b) a flexible retention member configured and dimensioned to extend through the retention passage and through the connecting passage and into the hole to help retain the projection in intramedullary engagement with said at least one of the portions of bone tissue.

2. The apparatus of claim 1 wherein the first surface extends completely through the main body from the third surface to the fourth surface.

3. The apparatus of claim 1 wherein the retention member has a first end portion, a second end portion, and an intermediate portion between the first and second end portions, the intermediate portion being disposed in the retention passage when the retention member is extending through the retention passage, the first and second end portions being engaged with each other to help retain the projection in intramedullary engagement with said at least one of the portions of bone tissue.

4. The apparatus of claim 3 wherein the first and second end portions are engaged with each other within the hole.

5. The apparatus of claim 1 wherein the main body includes a flange extending toward a central longitudinal axis of the hole and overlying a portion of the hole, the flange also overlying the first and second end portions of the retention member.

6. The apparatus of claim 1 wherein the projection is positioned at an angle relative to the main body.

7. The apparatus of claim 1 wherein the projection is positioned at an end of the main body.

8. The apparatus of claim 1 wherein the main body of the bone engagement member includes a sixth surface defining an aperture spaced from the hole for receiving a fastener.

9. The apparatus of claim 1 wherein the apparatus is an interphalangeal arthrodesis apparatus.

10. The apparatus of claim 1 wherein the retention member is a wire.

* * * * *